(12) United States Patent
Van Der Lugt et al.

(10) Patent No.: US 10,806,369 B2
(45) Date of Patent: *Oct. 20, 2020

(54) METHOD AND APPARATUS FOR DETERMINING THE POSITION OF A SURGICAL TOOL RELATIVE TO A TARGET VOLUME INSIDE AN ANIMAL BODY

(71) Applicant: Nucletron Operations B.V., Veenendaal (NL)

(72) Inventors: Wilco Van Der Lugt, Tiel (NL); Jeroen Schuurman, Amersfoort (NL); Johan Henning, Veenendaal (NL); Stefan Kwa, Utrecht (NL); Johann Kindlein, Toenisvorst (DE)

(73) Assignee: NUCLETRON OPERATIONS B.V., Veenendaal (NL)

( * ) Notice: Subject to any disclaimer, the term of this patent is extended or adjusted under 35 U.S.C. 154(b) by 588 days.

This patent is subject to a terminal disclaimer.

(21) Appl. No.: 15/646,033

(22) Filed: Jul. 10, 2017

(65) Prior Publication Data

US 2018/0008163 A1 Jan. 11, 2018

Related U.S. Application Data

(63) Continuation of application No. 13/347,225, filed on Jan. 10, 2012, now Pat. No. 9,730,608, which is a (Continued)

(30) Foreign Application Priority Data

Oct. 14, 2003 (EP) ..................................... 03078243

(51) Int. Cl.
*A61B 8/00* (2006.01)
*A61B 5/055* (2006.01)
(Continued)

(52) U.S. Cl.
CPC ............ *A61B 5/055* (2013.01); *G06T 11/008* (2013.01); *A61B 6/06* (2013.01); *A61B 8/12* (2013.01);
(Continued)

(58) Field of Classification Search
CPC ........... A61B 5/055; A61B 6/06; A61B 6/547; A61B 8/12; A61B 8/4461; A61B 8/483;
(Continued)

(56) References Cited

U.S. PATENT DOCUMENTS 5,095,908 A 3/1992 Belikan et al.
5,099,846 A 3/1992 Hardy
(Continued)

FOREIGN PATENT DOCUMENTS

EP 1070519 A1 1/2001
EP 1314452 A1 11/2001
WO WO 02/062224 A1 8/2002

*Primary Examiner* — Elmer M Chao
(74) *Attorney, Agent, or Firm* — Finnegan, Henderson, Farabow, Garrett & Dunner LLP (57) ABSTRACT

The invention relates to a method for determining the position of a surgical tool relative to a target volume inside an animal body according to a pre-plan comprising the steps of i) obtaining a plurality of two-dimensional images of said target volume using imaging means, each 2D-image being represented by an image data slice I(x,y,z); ii) reconstructing from said plurality of image data slices I(x,y,z) a three-dimensional image of said target volume using transformation means, said 3D-image being represented by a volumetric image data array V(x,y,z); iii) displaying said three-dimensional image of said target volume to an user using displaying means.

20 Claims, 5 Drawing Sheets

Related U.S. Application Data continuation of application No. 10/921,896, filed on Aug. 20, 2004, now Pat. No. 8,105,238.

(51) Int. Cl.
| | |
|---|---|
| *G06T 11/00* | (2006.01) |
| *A61B 6/06* | (2006.01) |
| *A61B 8/12* | (2006.01) |
| *A61B 17/00* | (2006.01) |
| *A61B 18/00* | (2006.01) |
| *A61N 5/10* | (2006.01) |
| *A61B 8/08* | (2006.01) |
| *A61B 90/00* | (2016.01) |

(52) U.S. Cl.
CPC ............. *A61B 8/4461* (2013.01); *A61B 8/483* (2013.01); *A61B 90/36* (2016.02); *A61B 2017/00274* (2013.01); *A61B 2018/00547* (2013.01); *A61N 5/1027* (2013.01); *A61N 5/1049* (2013.01); *A61N 2005/1011* (2013.01); *G06T 2211/428* (2013.01)

(58) Field of Classification Search
CPC .......... A61B 2017/00274; A61B 2018/00547; A61B 90/36; A61B 34/10; A61B 2090/374; A61B 2034/107; A61B 90/37; G06T 11/008; A61N 5/1049; A61N 5/1027; A61N 2005/1011
See application file for complete search history.

(56) References Cited

U.S. PATENT DOCUMENTS

| | | |
|---|---|---|
| 5,143,076 A | 9/1992 | Hardy et al. |
| 5,454,371 A | 10/1995 | Fenster et al. |
| 5,626,829 A | 5/1997 | Koutrouvelis |
| 5,842,473 A | 12/1998 | Fenster et al. |
| 5,868,757 A | 2/1999 | Koutrouvelis |
| 5,871,448 A | 2/1999 | Ellard |
| 5,938,583 A | 8/1999 | Grimm |
| 6,129,670 A | 10/2000 | Burdette et al. |
| 6,206,832 B1 | 3/2001 | Downey et al. |
| 6,610,013 B1 | 8/2003 | Fenster et al. |
| 6,701,176 B1 | 3/2004 | Halperin et al. |
| 2002/0045825 A1 | 4/2002 | Liu et al. |
| 2003/0135115 A1 | 7/2003 | Burdette et al. |
| 2004/0106869 A1 | 6/2004 | Tepper |

METHOD AND APPARATUS FOR DETERMINING THE POSITION OF A SURGICAL TOOL RELATIVE TO A TARGET VOLUME INSIDE AN ANIMAL BODY

This is a continuation of U.S. application Ser. No. 13/347,225, filed Jan. 10, 2012, which is a continuation of U.S. application Ser. No. 10/921,896, filed Aug. 20, 2004, now U.S. Pat. No. 8,105,238, issued Jan. 31, 2012, which claims priority of European Application No. 03078243.7, filed Oct. 14, 2003, all of which are incorporated herein by reference.

The invention relates to a method for determining the position of a surgical tool relative to a target volume inside an animal body according to a pre-plan comprising the steps of
i) obtaining a plurality of two-dimensional images of said target volume using imaging means, each 2D-image being represented by an image data slice I(x,y,z);
ii) reconstructing from said plurality of image data slices I(x,y,z) a three-dimensional image of said target volume using transformation means, said 3D-image being represented by a volumetric image data array V(x,y,z);
iii) displaying said three-dimensional image of said target volume to an user using displaying means.

The invention furthermore relates to an apparatus for determining the position of a surgical tool relative to a target volume inside an animal body according to a pre-plan comprising
    imaging means for obtaining a plurality of two-dimensional images of said target volume, each 2D-image being represented by an image data slice I(x,y,z);
    transformation means for reconstructing from said plurality of image data slices I(x,y,z) a three-dimensional image of said target volume represented by a volumetric image data array V(x,y,z);
    storing means for storing said plurality of image data slices I(x,y,z) and said volumetric image data array V(x,y,z);
    displaying means for displaying said three-dimensional image of said target volume to an user.

In the medical field, it is common to use imaging techniques to view internal organs of a subject. For example, in diagnosing prostate cancer, a diagnostician uses transrectal ultrasound (TRUS) to identify whether lesions are present as well as to determine the location, size and extent of lesions if present. Conventional diagnostic imaging equipment based on the principle of ultrasound typically comprise an ultrasound probe for transmitting ultrasound wave signals into the subject and receiving reflected ultrasound wave signals therefrom. The reflected ultrasound wave signals received by the ultrasound probe are processed and a two-dimensional image of the target volume under examination is formed.

A typical embodiment of an ultrasound probe is an intracavitary ultrasound probe primarily employed in the fields of gynaecology and obstetrics for the purpose of examining intrapelvic organs, such as the vagina, the uterus and the ovaries by women.

Another application, wherein intracavitary ultrasound probes are used, concerns the treatment of prostate cancer by implanting radioactive seeds through a hollow needle, which needle is inserted into the body near or in the prostate gland. An example of a device for effecting radiation therapy in an animal body by implanting radioactive seeds through a number of needles inserted in the animal body is for example disclosed in European patent application no. EP-A1-1 070 519. Prior to implanting the radioactive seeds, in that device one or more hollow needles are inserted into the animal body, wherein the exact location of the (tip of the) needle is monitored using images obtained with an intracavitary ultrasound probe, which probe is inserted into the patient's rectum. The insertion of the needles towards their desired pre-planned depth (location) is controlled using information obtained from said images. Another imaging technique is based on the principle of magnetic resonance imaging (MRI).

The above imaging techniques generate two-dimensional image slices of the target volume of the patient's body. Multiple 2D image slices spaced apart from each other on one longitudinal direction are necessary to obtain an overall view of the internal organs (the target volume) of the patient's body to be examined. There are several proposals to combine these multiple 2D image slices and to transform them into a three-dimensional image resulting in an overall 3D view of the target volume being imaged.

A 2D to 3D conversion technique based on for example ultrasound imaging and according to the above preamble is disclosed in U.S. Pat. No. 5,454,371.

It is an object of the invention to provide an improved method and apparatus utilizing a more sophisticated imaging technique to be used in combination with a pre-plan (for example a treatment plan).

According to the invention the method is characterized by the steps of
iv) selecting according to said pre-plan at least one specific imaginary target location within said three-dimensional image being displayed by said displaying means using selecting means;
v) controlling said imaging means relative to said target volume for obtaining in real time one two-dimensional image represented by an image data slice I(x,y,z) of a specific target location within said target volume corresponding to said specific imaginary target location being selected within said-three-dimensional image;
vi) displaying said real time two-dimensional images of said specific target location to the user using said displaying means; and
vii) determining the actual position of said surgical tool within said specific target location using said real time two-dimensional images of said specific-target location being displayed.

With these features an improved imaging technique is realised, wherein the diagnostician is capable in controlling the imaging means relative to the target volume of the animal body to be examined/viewed. The three-dimensional image thus obtained from the two-dimensional images serves as an imaginary working space for the diagnostician. Through manipulation within said imaginary 3D working space displayed to the diagnostician, the latter can easily manipulate the imaging means relative to the patient's body in order to obtain a real time or near real time two-dimensional image of the region of interest of the target volume.

Said region of interest of the target volume has to be selected within the imaginary 3D image and based on said selection the method according to the invention automatically focusses the imaging means on said region of interest of the target volume.

With this imaging technique according to the invention the diagnostician is capable of easily tracing the presence and position of a surgical tool relative to said target volume for example for treatment purposes. More in particular with this imaging technique the diagnostician is able to monitor the course of movement of said surgical tool relative to said target volume for example during insertion or navigation of said surgical tool through the animal body.

In a further improvement of the method according to the invention the method further characterized by the steps of viii) comparing said determined actual position of said surgical tool with a pre-planned desired position of said surgical tool relative to said target volume, and ix) correcting said determined actual position of said surgical tool in view of said pre-planned desired position by repositioning said surgical tool relative to said relative to a target volume.

Hence herewith the diagnostician is able to correct a sophisticated real time manner the course of movement of said surgical tool relative to said target volume.

Especially when operating the imaging technique according to the invention in combination with a certain pre-plan (for example a pre-planned radiation treatment plan for treating prostate cancer with radioactive sources) the method can be advantageously further characterized by the step of x) monitoring said correction step ix) until the actual position of said surgical tool corresponds with said pre-planned desired position.

The diagnostician is further supported in performing said imaging method according to the invention in combination with for example a pre-plan as the method is further characterized by the steps of xi) projecting according to said pre-plan during step iii) an imaginary surgical tool within said three-dimensional image being displayed, and xii) projecting within said three-dimensional image the actual position of said surgical tool as determined with step vii).

This provides a simple, but advantageous feedback control in the imaginary 3D working space of the diagnostician as the latter is herewith continuously visionally informed about the exact position of the surgical tool relative to the target volume in relation to the intended or desired position as pre-planned.

Moreover the method according to the invention involves the step of xiii) storing the image date obtained with steps i), ii) and/or v) using storing means.

The apparatus according to the invention is characterized by selecting means for selecting according to said pre-plan at least one specific imaginary target location within said three-dimensional image being displayed by said displaying means; control means for controlling said imaging means relative to said target volume for obtaining in real time one two-dimensional image, represented by an image data slice I(x,y,z), of a specific target location within said target volume corresponding to said specific imaginary target location being selected within said three-dimensional image; and means for determining the actual position of said surgical tool within said specific target location using said real time two-dimensional images of said specific target location.

When using the apparatus according to the invention controlling the imaging means relative to the target volume of the animal body to be examined/viewed is allowed. Instead of directly controlling the imaging means relative to the target volume for example by direct manipulation of the imaging means in a specific orientation relative to the target volume, said manipulation is now performed in a remote manner. The three-dimensional image obtained from the two-dimensional images serves as an imaginary working space for the diagnostician.

Through manipulation within said imaginary 3D working space being displayed, the diagnostician is able to orientate, to redirect as well as to operate the imaging means relative to the patient's body in a remote manner in order to obtain a real time or near real time two-dimensional image of the region of interest of the target volume.

Direct operation of the imaging means is no longer necessary and an easy tracing of the presence and/or position of a surgical tool relative to said target volume for example for treatment purposes is herewith possible. More in particular with this imaging technique the diagnostician is able to monitor the course of movement of said surgical tool relative to said target volume for example during insertion or navigation of said surgical tool through the animal body.

In an improved embodiment of the apparatus according to the invention allowing in a sophisticated real time manner the correction of the course of movement of said surgical tool relative to said target volume comparison means are present for comparing said determined actual position of said surgical tool with a desired position of said surgical tool as pre-planned and also correcting means are present for correcting said determined actual position in view of said pre-planned desired position by repositioning said surgical tool relative to said relative to a target volume. These features are especially suited when implementing the apparatus according to the invention in combination with a certain pre-plan (for example a pre-planned radiation treatment plan for treating prostate cancer with radioactive sources).

More in particular an improved operation of the apparatus according to the invention is obtained as displacement means are present for displacing said imaging means relative to said target volume based on said control means.

Especially said displacement means are capable of displacing said imaging means in a longitudinal and/or a rotational direction resulting in an advantageous control of the imaging means in relation to the pre-plan.

As suitable imaging means ultrasound imaging means, for example a rectal ultrasound imaging probe or magnetic nuclear imaging means can be used with the apparatus according to the invention.

When using magnetic resonance imaging the control means of the apparatus according to the invention are arranged for energizing the appropriate gradient coils of the magnetic nuclear imaging means. This allows an improved control of the imaging means depending on the region of interest to be imaged as selected by the diagnostician in the imaginary three-dimensional working space.

More in particular said selection means comprise a display pointer, a mouse pointer or an input device, like a keyboard.

Various surgical tools can be used when operating the apparatus according to the invention. For example said surgical tool can be at least one implant needle and/or at least one radiation emitting source, for example a radioactive brachytherapy seed or HDR source being inserted through an implant needle. With these types of surgical tools the apparatus (and method) according to the invention as very suitable for use in brachytherapy treatments (e.g. the treatment of prostate cancer).

Figure 1:
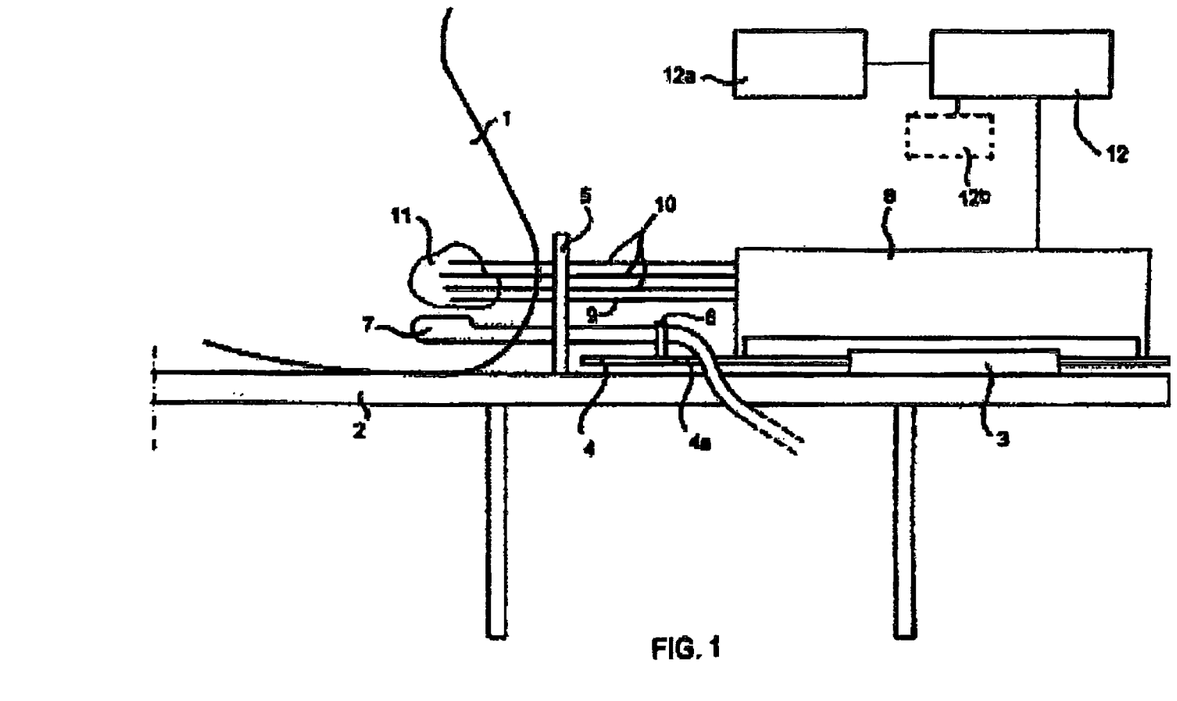
FIG. 1 shows in very schematic form a known radiation treatment device using imaging means.

The invention will now be described in combination with a drawing, which drawing shows in:

FIG. 1 shows in very schematic form various elements of a known radiation treatment device using a template-assembly for implanting one or more energy emitting sources, e.g. radioactive seeds towards a desired location within an animal body, for example into a prostate gland using ultrasound imaging means.

The known device shown in FIG. 1 operates as follows. A patient 1 is under spinal or general anaesthesia and lies on the operating table 2 in lithotomy position. The (ultrasound) imaging probe 7 is introduced into the rectum and the probe is connected via signal line 7a with a well known image screen, where an image may be seen of the inside of the patient in particular of the prostate gland 11 as seen from the point of view of the imaging probe 7. The template assembly 5 is attached to the stepping device 4, thereby insuring the correlation of the ultrasound image geometry and the template-assembly 5. Subsequently further needles 10 are introduced in the body and the prostate gland under ultrasound guidance one by one.

Moving the imaging probe with the drive means 4 longitudinally within the rectum controls the needle depths of each needle 10. After all needles 10 have been placed, their positions relative to the prostate gland 11 are determined in at least one of several known ways. In a known way the therapy planning module 12a determines how the needles 10 are to be placed in the prostate and how many radiation emitting sources are to be placed in what order in each of the needles 10. The information about the desired placement of the radioactive seeds in the needles 10 is used to control the seed loading unit 8.

Figure 2:
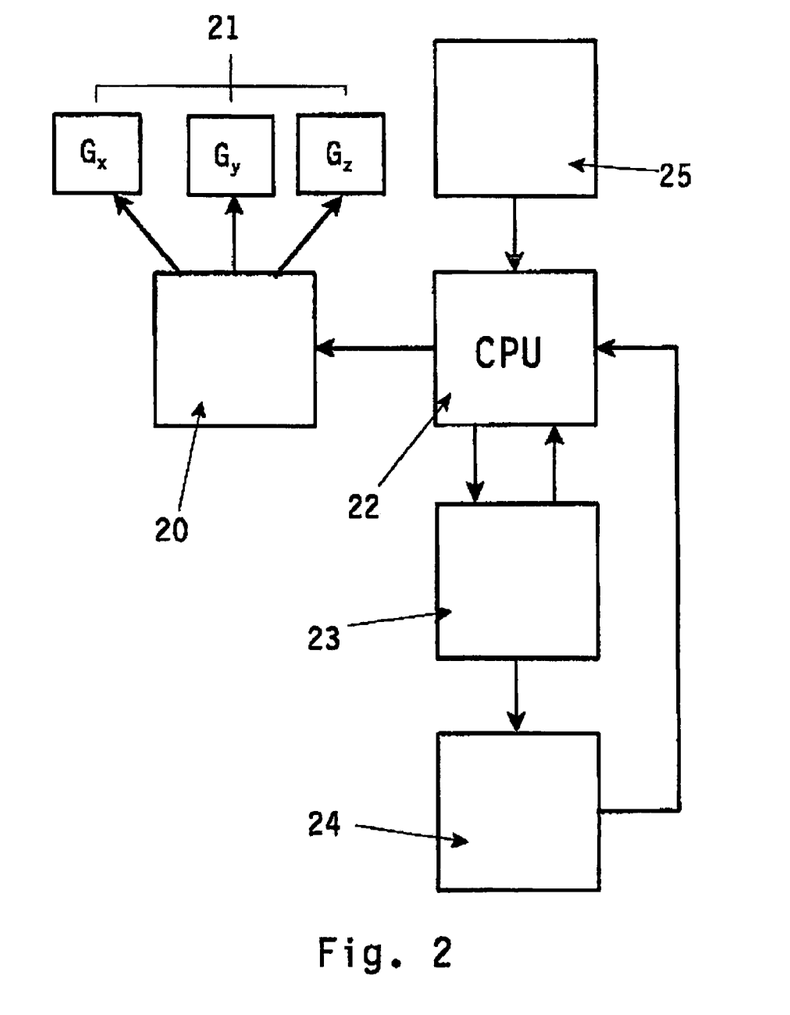
FIG. 2 a block diagram depicting a first embodiment of the method according to the invention.
Figure 3:
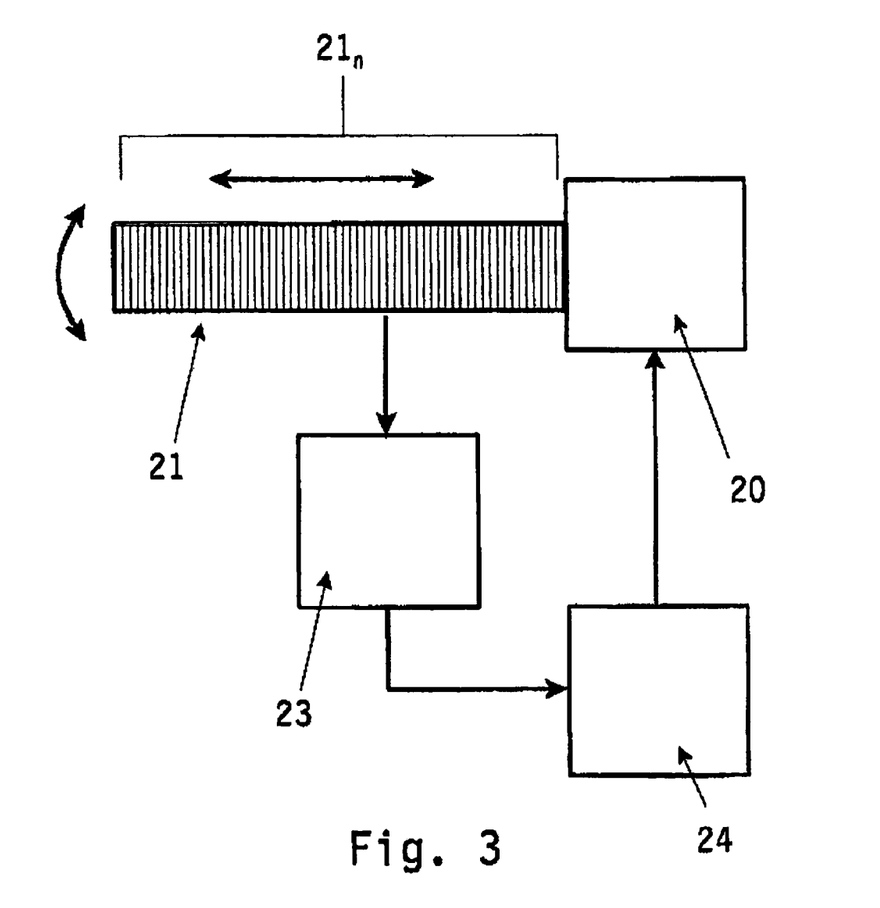
FIG. 3 a block diagram depicting a second embodiment of the method according to the invention.

FIGS. 2 and 3 disclose a block diagram depicting a first and a second embodiment of the method according to the invention. In the Figures with reference numeral 20 imaging means are depicted, which in FIG. 2 consists of imaging means based on magnetic resonance imaging. The MRI means depicted with reference numeral 20 in FIG. 2 generally comprises a power source for energizing the gradient coils $G_x$, $G_y$, $G_z$. The gradient coils are in FIG. 2 depicted with reference numeral 21 ($G_x$-$G_y$-$G_z$).

When independently energized, the three gradient coils produce a linearly variable magnetic field in any direction, where the net gradient is equal to $\sqrt{(G_x^2+G_y^2+G_z^2)}$. With an appropriate design, the gradient coils $G_x$, $G_y$, $G_z$ create a magnetic field, that linearly varies in strength versus distance over a predefined field of view. When superimposed upon a homogeneous magnetic field $B_o$ not shown in the figures positive fields add to $B_o$ and negative gradient fields reduce $B_o$.

The resulting gradient is linear, position-dependent and it causes protons to alter their precessional frequency corresponding to their position along the applied gradient in a known and predictable way. Any gradient direction is possible by superimposition of the three MRI involves RF excitations at the Larmor-frequency of the protons combined with magnetic field gradients to localize the signal from each individual volume element after the excitation.

The MR imaging means 20 are connected to a central processing unit CPU 22 intended for operating the imaging means 20.

Central processing unit 22 interacts with transformation means 23, which means include digitizer and image processing units for digitizing and further processing the two-dimensional images generated by said imaging means 20.

Hereto the transformation means 23 may include storage means (for example physical memory) for storing the two-dimensional images obtained from the imaging means 20 as 2D information. The transformation means 23 capture and digitize the two-dimensional information transfers the 2D information to a computer system 24 for planning and visualisation purposes. Also in computer system 24 said two-dimensional image information is transformed into a three-dimensional image of the target volume being imaged.

Said computer system 24 may include planning software for pre-planning for example a radioactive treatment on the target volume being imaged by imaging means 20.

Figure 4:
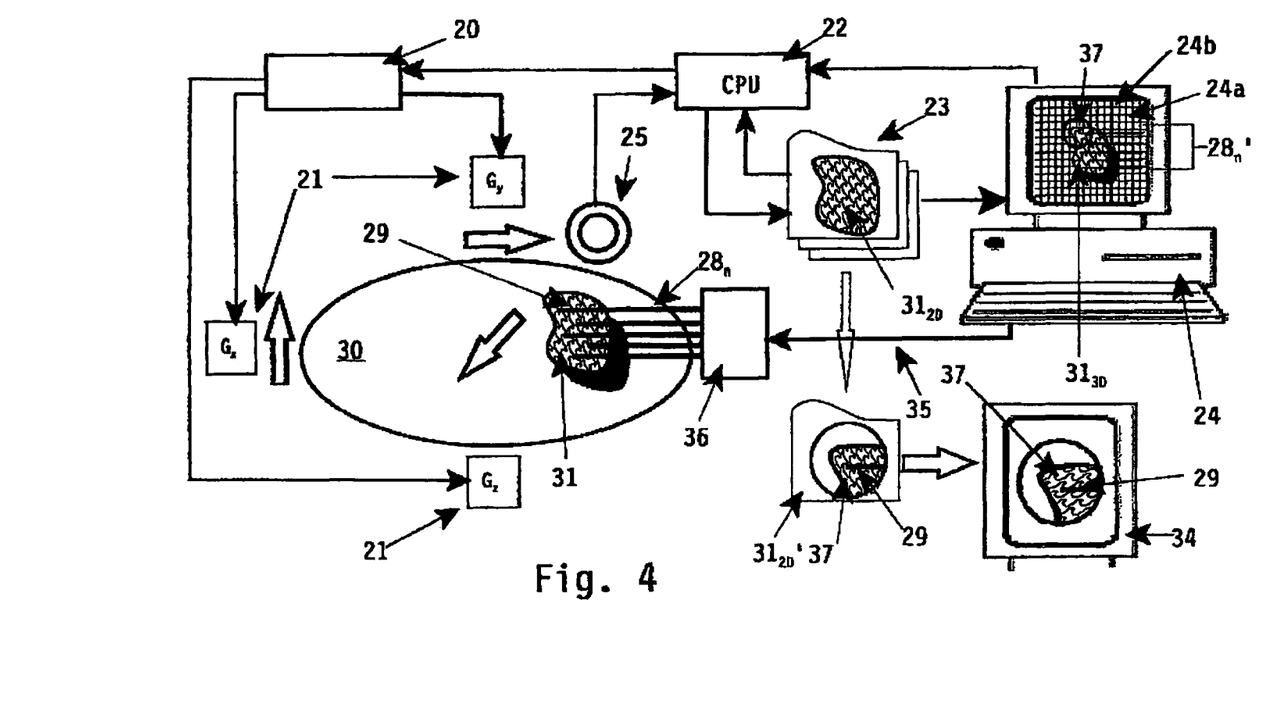
FIG. 4 a more detailed embodiment of an apparatus according to the invention.

As will be elucidated in more detail with reference to FIG. 4 the method according to the invention is further characterized in that within said three-dimensional image being visualized in said computer system 24 a specific imaginary target location is to be selected using suitable selecting means. Upon said selection in said computer means 24 the central processing unit 22 is provided with control signals from said computer system 24, which CPU 22 in turn controls the MR imaging means 20 for obtaining a two-dimensional image in which image the target location within the target volume corresponding with the imaginary target location selected within said three-dimensional image is obtained.

In FIG. 3 the method according to the invention is described using an ultrasound probe 20 having an ultrasound transducer 21 which may consists of multiple ultrasound transducer elements $21_n$. The ultrasound probe 20 is provided with drive means (not shown) for displacing the transducer element 21 in longitudinal direction or in rotational direction relative to the target volume to be imaged.

Ultrasound wave signals emitted by the transducer element 21 towards the target volume to be examined are orientated in a physical interaction field that intersects the target volume to be imaged as a slice. Within said physical interaction field the ultrasound wave signals can be transmitted, absorbed or reflected dependent on the composition of the tissue.

The reflected ultrasound wave signals are received by the transducer element 21 and fed to an ultrasound processing unit (transformation means) 23 for generating a two-dimensional image corresponding to the physical interaction field (image slice) of the target volume. By rotating the transducer element 21 multiple two-dimensional image slices spaced apart from each other are obtained.

As in FIG. 2, also in FIG. 3 unit 24 transforms these two-dimensional image slices into a three-dimensional image, which is used by said computer system 24 for planning and visualisation purposes.

By selecting an imaginary target location within said three-dimensional image being displayed by said computer system 24 control signals are generated and fed to the control means of the ultrasound probe 20. Based on said control signals the transducer element 21 is displaced in longitudinal or rotational orientation relative to the target volume such that the physical interaction field of the ultrasound wave signals propagating towards the target volume corresponds with the imaginary target location selected within said three-dimensional image.

Hence one two-dimensional image is obtained of said specific target location within the target volume corresponding with the imaginary target location selected within said three-dimensional image.

In FIG. 4 a more detailed embodiment of an apparatus implementing the method according to the invention is disclosed. For a proper understanding likewise parts are described with identical reference numerals.

In FIG. 4 reference numeral 30 depicts schematically an animal body (a patient), whereas reference numeral 31 depicts the target volume under examination, for example an internal organ contained in said animal body 30. Referring to FIG. 1 said organ 31 can be the prostate gland of a male person 30, which person has to undergo a radioactive therapy treatment session by implanting—using multiple implant needles $28_n$—one or more energy emitting sources, for example radioactive seeds, through said implant needles $28_n$ at desired locations within the prostate 31.

For performing the imaging technique as used with the method and apparatus according to the invention magnetic resonance imaging means 20 (MRI) are used. As already described in FIG. 2 each MRI means comprise multiple gradient coils 21 ($G_x$, $G_y$, $G_z$), which coils can be energized or activated separately depending on the image acquisition to be performed.

The method and apparatus according to the invention are based on the imaging technique to obtain a three-dimensional image of a specific target volume 31 inside an animal body 30 by generating a plurality of two-dimensional image slices $31_{20}$ with a proper operation of the imaging means 20.

For obtaining multiple two-dimensional image slices $31_{20}$ the gradient coils 21 ($G_x$, $G_y$, $G_z$) are controlled in a such manner that a physical interaction field intersecting or slicing the target volume 31 corresponding with an image slice is created.

The magnetic field and RF created by said magnetic resonance imaging means interact with the tissue of the target volume 31 in said physical interaction field. The interaction between the magnetic field generated by the gradient coils 21 ($G_x$, $G_y$, $G_z$) is collected by a receiver coil 25 of the magnetic resonance imaging means 20 resulting in a two-dimensional image corresponding with the visual representation of the target volume 31 within said slice (physical interaction field).

A plurality of two-dimensional image slices $31_{20}$ are collected and stored in suitable storage means in a processing unit 33. The plurality of two-dimensional image slices $31_{20}$ are transformed by computer system 24 using suitable transformation means into a three-dimensional image of the target volume 31. The three-dimensional image is stored within computer system 24 and displayed on a display 24a (reference numeral $31_{30}$).

This transformation technique for generating a three-dimensional image from a plurality of two-dimensional image slices is known in the art.

According to the invention it is intended to manipulate the imaging means 20 by selecting a specific imaginary target location 37 within the three-dimensional image $31_{30}$ being displayed on display 24a. The target location being selected is in FIG. 4 depicted with a circle 37. The selection of said imaginary target location 37 can be performed using specific selection means like for example a mouse pointer a display pointer (for example a light pen) or an other suitable input device like a computer keyboard.

The selection of the specific imaginary target location or region 37 triggers or activates control means 22 (central processing unit) for controlling the imaging means 20. In FIG. 4, due to the selection of specific target region 37 within the imaginary three-dimensional image $31_{30}$ the magnetic resonance imaging means 20 are controlled/activated such that the gradient coils 21 ($G_x$, $G_y$, $G_z$) are activated such, that one two-dimensional image $31_{20}'$ of said imaginary target region 37 as selected is obtained via transformation means 23 where said single two-dimension image slice is imaged and digitized for further displaying purposes.

This digitized two-dimensional image $31_{20}'$ is displayed to the user (diagnostician) using display means 34. Said display means 34 can be a separate display device being part of transformation means 23, but it can also be implemented in the display 24b of the computer system 24. In the latter case display 24b is divided in several sub-windows, wherein each sub-window is used for displaying the three-dimensional image $31_{30}$ or the single two-dimensional image $31_{20}'$ of the specific target region 37 as selected in said three-dimensional image $31_{30}$ respectively.

Figure 5:
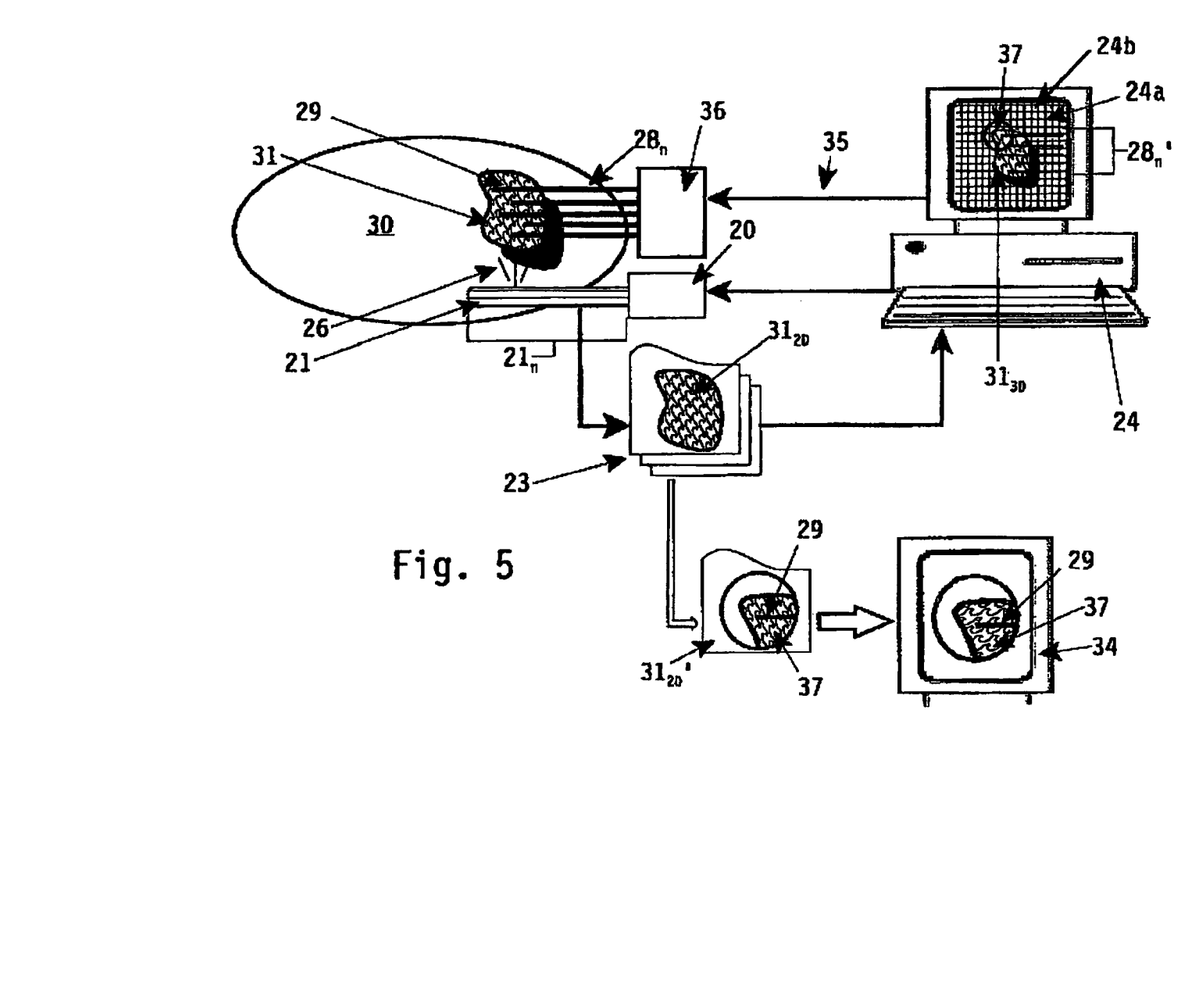
FIG. 5 a further more detailed embodiment of an apparatus according to the invention.

In a likewise manner is it possible to implement the method and apparatus in combination with ultrasound imaging means as depicted in FIG. 5. In this FIG. 5 ultrasound image slice are produced using the transducer elements $21_n$ of the ultrasound probe 20. Said probe 20 is—like in FIG. 1—inserted into the rectum of a male patient 30 for ultrasound imaging of the internal organs and more in particular the prostate gland 31.

Ultrasound wave signals 26 are transmitted by the transducer elements $21_n$ (of ultrasound transducer 21) towards the prostate gland 31 (target volume) and reflected ultrasound wave signals are received therefrom. The reflected ultrasound wave signals received by the ultrasound probe 20 are processed by the ultrasound processing unit (transformation means) 23 and a two-dimensional image of the target volume under examination is formed. By rotating the ultrasound probe 20 (the ultrasound transducer 21) relative to the target volume subsequent two-dimensional image slices $31_{20}$ are obtained and processed by ultrasound processing unit (transformation means) 23.

The transformation means 23 capture and digitize the two-dimensional image information and transfers the 2D information to a computer system 24 for planning and visualisation purposes. Also in computer system 24 said plurality of two-dimensional image slices $31_{20}$ are transformed into a three-dimensional image $31_{30}$ of the target volume 31 being imaged. Said computer system 24 may include planning software for pre-planning for example a radioactive treatment on the target volume 31 being imaged by imaging means 20.

Similar to the embodiment of FIG. 4 the ultrasound imaging probe 20 can be manipulated by selecting a specific imaginary target location 37 within the three-dimensional image $31_{30}$ being displayed on display 24a. The target location being selected is in FIG. 5 depicted with a circle 37.

Due to the selection of the specific imaginary target location or region 37 the ultrasound probe 20 is controlled by computer system 24. The ultrasound transducer 21 can be displaced in longitudinal and rotation manner relative to the target volume 31 in order to create a psychical interaction field through the target volume 31 corresponding to the selected imaginary target location 37. The re-orientation of the ultrasound transducer 21 relative to the target volume generates one two-dimensional image $31_{20}'$ of said imaginary target region 37 as selected. Said single two-dimensional image $31_{20}'$ is captured and digitized by transformation means 23 for further displaying purposes.

This digitized two-dimensional image $31_{20}'$ is displayed to the user (diagnostician) using display means 34. Said display means 34 can be a separate display device being part of transformation means 23, but it can also be implemented in the display 24b of the computer system 24. In the latter case display 24b is divided in several sub-windows, wherein each sub-window is used for displaying the three-dimensional image $31_{30}$ or the single two-dimensional image $31_{20}'$ of the specific target region 37 as selected in said three-dimensional image 31" respectively.

Hence with the method and apparatus according to the invention it is possible to control the imaging means 20 (MRI or ultrasound) in an indirect remote manner by selecting an image direction in the three-dimensional image of the target volume 31 within the animal body 30. An user can control the magnetic resonance imaging means 20 from behind display 24a using the computer system 24 and control means 22.

This imaging technique is beneficial for example medical applications using a pre-plan, for example a pre-planned therapy treatment and more in particularly for use with the brachytherapy treatment of prostate cancer using the device as depicted in FIG. 1.

For a treatment of prostate cancer using multiple implant needles $28_n$ to be inserted inside a prostate gland 31 of a male person 30 the desired, pre-planned location/depth of the multiple implant needles $28_n$ is pre-planned according to a desired-treatment therapy using known treatment planning software contained for example in computer system 24. The implant needles $28_n$ are considered a surgical tool, and are displayed as imaginary surgical tools $28_n{'}$ and projected on said three-dimensional image $31_{30}$ of the prostate gland 31.

Likewise it is possible to project a frame 24b of vertical and horizontal lines on said three-dimensional image $31_{30}$, which frame 24b may correspond with aperture or grid orientation on template-assembly 5 as depicted in FIG. 1. By selecting a specific grid position within frame 24b a specific implant needle $28_1$ (for example the implant needle depicted with reference numeral 29) is selected and its insertion through the animal body 30 towards its desired, pre-planned depth within the prostate gland 31 can be monitored with the single two-dimensional image $31_{20}{'}$.

The selection of the grid position within frame 24b corresponding with specific implant needle 29 leads to a remote control of imaging means 20 via control means 22 resulting in one two-dimensional image $31_{20}{'}$ depicting the image slice intersecting with said grid position.

As with this imaging technique the insertion of the specific implant needle 29 can be monitored in real-time it is possible to control via control line 35 the needle insertion means 36 until said implant needle 29 reaches its desired, pre-planned depth relative to the prostate gland 31.

Subsequent energy emitting sources, for example radioactive seeds, can be inserted through said implant needle 29 for performing a radioactive therapy treatment as pre-planned using planning software contained in computer system 24.

The invention claimed is:

1. A surgical imaging method for determining and displaying, within a computer-generated display of a display device, a current position of a surgical tool relative to a planned position of the surgical tool within a patient, the surgical imaging method comprising:
   obtaining, via an imaging device, a three-dimensional image of a target volume within the patient;
   generating a first display signal causing the display device to display the three-dimensional image of the target volume on the display device, wherein the displayed three-dimensional image includes a three-dimensional representation of the surgical tool inserted in the target volume at a position corresponding to at least one planned position of the surgical tool;
   receiving a user selection, based on user interaction with the three-dimensional image on the display device, that identifies a selected location in the displayed three-dimensional image;
   generating, responsive to receiving the user selection that identifies the selected location in the displayed three-dimensional image, a control signal causing the imaging device to capture a corresponding location on the patient that corresponds to the selected location in the displayed three-dimensional image;
   obtaining, via the imaging device, a two-dimensional image of the corresponding location on the patient;
   generating a second display signal causing the display device to display the two-dimensional image including an image representation of the surgical tool at the current position in the patient; and
   wherein the second display signal is configured to display a visual feedback, via the display device, that indicates the current position of the surgical tool in the patient relative to the planned position of the surgical tool.

2. The method of claim 1, wherein the selected location corresponds to the planned position of the surgical tool.

3. The method of claim 1, further comprising determining an actual position of the surgical tool.

4. The method of claim 3, further comprising:
   comparing the actual position of the surgical tool to the planned position of the surgical tool; and
   providing data including instructions to modify treatment, based on the comparison, to correspond to the planned position.

5. The method of claim 1, wherein the displayed three-dimensional image of the target volume includes a three-dimensional representation of an imaginary surgical tool inserted in the target volume at a position corresponding to the planned position of the surgical tool.

6. The method of claim 1, wherein the three-dimensional image of the target volume is displayed using a grid orientation.

7. The method of claim 6, wherein the user selection of the selected location further includes grid positions of the three-dimensional image on the grid orientation.

8. The method of claim 6, wherein the grid orientation is projected using a plurality of vertical and horizontal lines.

9. The method of claim 5, wherein obtaining the two-dimensional image further includes adjusting the imaging device, based upon the control signal, to obtain the two-dimensional image of the selected location.

10. The method of claim 1, wherein the visual feedback comprises an image overlay of the image representation of the surgical tool at the current position and the representation of the surgical tool at the planned position.

11. A surgical imaging apparatus for determining and displaying, within a computer-generated display of a display device, a current position of a surgical tool relative to a planned position of the surgical tool within a patient, the surgical imaging apparatus comprising:
   an imaging device configured to obtain a three-dimensional image of a target volume within the patient;
   a display of a computer system configured to display the three-dimensional image of the target volume within the patient, wherein the displayed three-dimensional image includes a three-dimensional representation of the surgical tool inserted in the target volume at a position corresponding to the planned position of the surgical tool;
   a selector configured to interact with the three-dimensional image on the display of the computer system to select at least one selected location in the displayed three-dimensional image; and a controller connected to the imaging device configured to:

generate, responsive to the selector selecting at least one selected location in the displayed three-dimensional image, a control signal causing the imaging device to capture a corresponding location on the patient that corresponds to the selected location in the displayed three-dimensional image;

control the imaging device to obtain a two-dimensional image of the corresponding location on the patient; and generate a second display signal for displaying the two-dimensional image including an image representation of the surgical tool at the current position in the patient, wherein the second display signal is configured to display, via the display device, visual feedback that indicates the current position of the surgical tool in the patient relative to the planned position.

12. The apparatus of claim 11, wherein the imaging device comprises a magnetic resonance imaging device.

13. The apparatus of claim 12, further including a displacer configured to adjust the imaging device based on the control signal.

14. The apparatus of claim 13, further including a driver configured to adjust the position of the surgical tool to correspond with the planned position of the surgical tool.

15. The apparatus of claim 11, wherein the display is configured to display the three-dimensional image of the target volume with a grid orientation.

16. The apparatus of claim 15, wherein the grid orientation is projected using a plurality of vertical and horizontal lines.

17. The apparatus of claim 16, wherein the selector is configured to select the target region by specifying grid positions of the three-dimensional image on the grid orientation.

18. The apparatus of claim 11, wherein the surgical tool comprises at least one radioactive brachytherapy seed or high dose rate (HDR) source.

19. The apparatus of claim 18, further comprising an inserter for inserting the at least one radioactive seed or HDR source through the surgical tool for performing a radioactive therapy treatment.

20. The apparatus of claim 11, wherein the user selection is received from a display pointer, a mouse pointer, or a keyboard.

* * * * *